United States Patent [19]
Kiefer et al.

[11] Patent Number: 5,641,909
[45] Date of Patent: Jun. 24, 1997

[54] SCAN ASSEMBLY STRUCTURE

[75] Inventors: Karl F. Kiefer, Woodlands; Gerard T. Pittard, Houston, both of Tex.; Donald L. Chaffee, Park City, Utah; C. Grissom Steele; Terry P. Clifton, both of Houston, Tex.

[73] Assignee: Gas Research Institute, Chicago, Ill.

[21] Appl. No.: 222,621

[22] Filed: Apr. 5, 1994

[51] Int. Cl.$^6$ .................................................. G01N 29/04
[52] U.S. Cl. ........................... 73/623; 73/637; 73/638; 73/639
[58] Field of Search ........................ 73/623, 622, 635, 73/637, 638, 639, 640

[56] References Cited

U.S. PATENT DOCUMENTS

| | | | |
|---|---|---|---|
| 2,723,357 | 11/1955 | Van Valkenburg et al. | 73/623 |
| 3,714,816 | 2/1973 | Miller | 73/71.5 |
| 3,763,694 | 10/1973 | Rathburn | 73/71.5 |
| 4,055,990 | 11/1977 | Topping | 73/623 |
| 4,131,018 | 12/1978 | Müller et al. | 73/623 |
| 4,285,243 | 8/1981 | Collingwood | 73/623 |
| 4,289,025 | 9/1981 | Norel et al. | 73/639 |
| 4,302,976 | 12/1981 | Bull | 73/639 |
| 4,304,134 | 12/1981 | Rouse et al. | 73/634 |
| 4,506,549 | 3/1985 | Thome | 73/623 |
| 4,615,218 | 10/1986 | Pagano | 73/639 |
| 4,621,532 | 11/1986 | Takagi et al. | 73/623 |
| 4,691,572 | 9/1987 | van den Berg et al. | 73/643 |
| 4,718,277 | 1/1988 | Glascock | 73/622 |
| 4,735,087 | 4/1988 | Hourani et al. | 73/597 |
| 4,769,598 | 9/1988 | Krieg et al. | 73/623 |
| 5,007,291 | 4/1991 | Walters et al. | 73/640 |
| 5,014,711 | 5/1991 | Nagasaki | 128/660.7 |
| 5,046,033 | 9/1991 | Andreasen et al. | 364/580 |
| 5,170,346 | 12/1992 | Crawford et al. | 364/413 |
| 5,204,622 | 4/1993 | McCaslin et al. | 376/245 |
| 5,254,944 | 10/1993 | Holmes et al. | 73/623 |

Primary Examiner—Hezron E. Williams
Assistant Examiner—Rose M. Finley
Attorney, Agent, or Firm—Hopkins & Thomas; Scott A. Horstemeyer

[57] ABSTRACT

Apparatus is disclosed for providing one hundred percent inspection of natural gas mains under operating flow conditions. The apparatus includes a scan unit assembly which is inserted into the gas main to collect data for the production of graphic images of the wall of the gas main. The scan unit includes a plurality of scan rollers, each containing an ultrasonic transducer, which traverse the surface of the wall defining the inner diameter of the gas main. The ultrasonic transducers transmit interrogating pulses into the wall of the gas main at a pre-determined spaced apart interval resulting in a helical scan pattern of interrogating pulses. The return pulses from the surfaces defining the inner diameter and outer diameter of the gas main and any imperfections and/or flaws within the wall of the main are received by the transducer and transmitted to a display unit for a visual indication (a tomograph) of the wall of the gas main.

18 Claims, 6 Drawing Sheets

Ⓐ NORMAL RETURN FROM THE I.D.

Ⓑ NORMAL RETURN FROM O.D.

Ⓒ LATE RETURN - INCREASE IN DIA.

Ⓓ NORMAL RETURN - STANDARD O.D.

Ⓔ NORMAL RETURN - STANDARD I.D.

Ⓕ EARY RETURN - DECREASED DIA. O.D.

Ⓖ NORMAL RETURN - STANDARD I.D.

Ⓗ EARLY RETURN - DECREASE O.D. OR INCLUSION

Ⓘ NORMAL RETURN - STANDARD O.D.

FIG. 12

SCAN ASSEMBLY STRUCTURE

TECHNICAL FIELD

The present invention relates, in general, to apparatus for inspecting buried natural gas mains, and, more particularly, to apparatus for inspecting such gas mains under operating flow conditions.

BACKGROUND OF THE INVENTION

Thousands of miles of buried natural gas mains of varying sizes and formed from various materials are presently in service. All of these mains are in some state of progressive degradation. In most instances, the extent of such degradation is unknown, and hence, the serviceability of the mains is similarly unknown. This lack of information with respect to degree of degradation results in unforseen gas main breaks and/or leaks, and necessitates the expending of substantial time and expense in locating these defects so that repairs and/or replacement can be made. Because of the need to detect conditions which might result in gas main breaks and/or leaks, apparatus has been developed for inspecting gas mains, and such apparatus is usually referred to as a pipe line "pig". Such pipe line "pigs" typically include a housing with a plurality of sensors mounted on the outer surface thereof in a pre-determined configuration or array to contact the inner surface of the gas main. Since the sensors are in a pre-determined configuration or array, one hundred percent inspection of the wall of the gas main is generally not possible, i.e., the portion of the wall between two adjacent sensors is typically not inspected. Achieving one hundred percent inspection of the wall of the gas main by utilizing such apparatus is generally not possible, and to approach one hundred percent inspection of the wall would require an inordinate number of sensors.

In view of the foregoing, it has become desirable to develop apparatus that provides one hundred percent inspection of the walls of gas mains under operating flow conditions and a method of assessing the serviceability of buried gas mains and recording the data for future reference and analysis. With this capability, natural gas utilities can monitor the rate of degradation of gas mains and plan repairs and/or replacements before failures occur.

SUMMARY OF THE INVENTION

The present invention provides one hundred percent inspection of the walls of gas mains under operating flow conditions through the use of a unique scanning unit which is inserted into working gas mains to collect dam for production of graphic images of the wall forming the gas main. The scanning unit includes stationary front and rear units with a sensor section interposed therebetween. Both the front and rear units are provided with wheels which are angularly positioned approximately 90° relative to one another and oriented so that the direction of travel of the scanning unit is along the longitudinal axis of the gas main. The wheels are coupled to position sensors that provide data as to the location of the scanning unit as it travels down the main. Two scan rollers are attached to or received within the sensor section and are angularly positioned 180° relative to one another. In one embodiment, the scan rollers are canted in the direction of travel of the scanning unit through the gas main and propel the unit through the main. In an alternate embodiment, an external force must be applied to the scanning unit to move the unit through the main. In both embodiments, each scan roller is positioned substantially perpendicular to the longitudinal axis of the scanning unit and contains an ultrasonic transducer which directs an interrogating pulse into the wall of the gas main at a pre-determined angularly spaced-apart interval. The interrogating pulses form a helical scan pattern. The return pulses (reflective pulses) from the surfaces defining the inner diameter and outer diameter of the gas main and any imperfections or flaws within the wall of the main are received by the transducer, converted into digital form, and are subsequently transmitted to a surface unit which produces a tomograph of the wall of the gas main. In essence, a model of the condition of the surfaces defining the inner diameter and outer diameter of the gas main and a cross-sectional view of the wall of the gas main is generated over the length of the main.

An object of the present invention is to provide apparatus for one hundred percent inspection of the walls of gas mains under operating flow conditions.

Another object of the present invention is to provide apparatus for inspecting the walls of gas mains and which propels itself through the gas main.

A further object of the present invention is to provide apparatus for inspecting the walls of gas mains by utilizing a helical scan technique permitting the condition of the wall to be displayed in tomographic form.

A still another object of the present invention is to provide apparatus for inspecting the walls of gas mains by utilizing ultrasonic techniques to determine the dimensions of the inner diameter and outer diameter of the gas main and to locate any imperfections and/or flaws within the walls of the gas main.

3

DESCRIPTION OF THE PREFERRED EMBODIMENT

Figure 1:
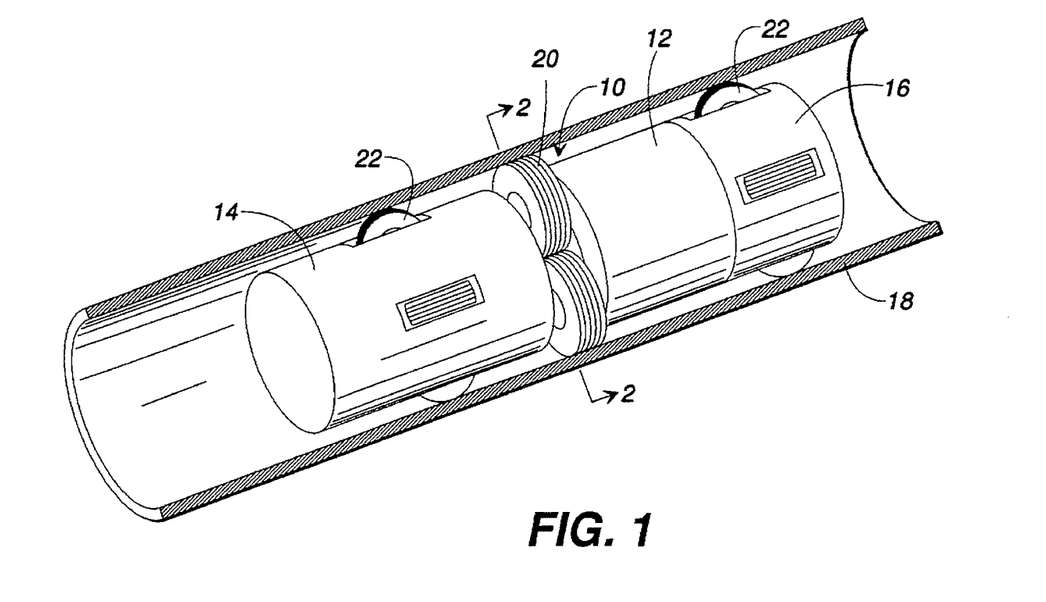
FIG. 1 is a perspective view, partially broken away in cross-section, of a first embodiment of the scan unit assembly of the present invention.

Referring now to the drawings where the illustrations are for the purpose of describing the preferred embodiment of the present invention and are not intended to limit the invention described herein, FIG. 1 is a perspective view of a first embodiment of the scan unit assembly 10 of the present invention. The scan unit assembly 10 includes a sensor section 12 interposed between a front section 14 at one end of the assembly 10 and a rear section 16 at the other end thereof. The scan unit assembly 10 is receivable within the gas main 18 to be inspected and is movable therein along the longitudinal axis of the main 18. The sensor section 12 includes a pair of scan rollers 20 which are angularly positioned approximately 180° relative to one another and canted slightly in the direction of travel through the gas main 18 to drive the scan unit assembly 10 therethrough. This canting or offsetting of the scan rollers 20 causes the scan unit assembly 10 to "pull" itself through the gas main 18 as the scan rollers 20 rotate. The front section 14 and the rear section 16 of the scan unit assembly 10 are provided with wheels 22 which are angularly positioned approximately 90° relative to one another in each unit 14, 16, and are oriented along the longitudinal axis of the assembly 10. The wheels 22 are coupled to rotation position sensors (not shown) so that movement of the scan unit assembly 10 within the gas main 18 and the location of the scan unit assembly 10 therein can be accurately monitored. Biasing means (not shown) are provided and apply a radially outwardly directed force to each of the wheels 22 permitting the scan unit assembly 10 to be used within gas mains 18 of various inner diameters.

Figure 2:
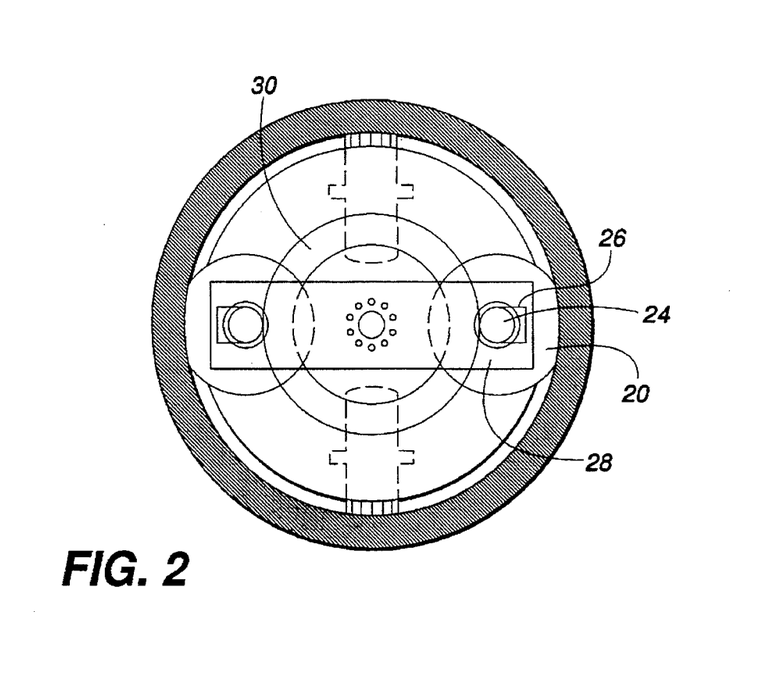
FIG. 2 is a partial cross-sectional view of the scan unit assembly taken across section-indicating lines 2—2 in FIG. 1.

Referring now to FIG. 2, an axle 24 about which a scan roller 20 rotates is received within an elongated slot 26 provided in either end of a crank arm 28 which is rotated by a scan motor 30 located within front section 14 of scan unit assembly 10. The elongated slots 26 permit radial movement of the scan roller 20 therein. Biasing means (not shown) are provided and apply a radially outwardly directed force to the axle 24 and the scan roller 20 causing the scan roller 20 to grippingly engage the surface defining the inner diameter of the wall of the gas main 18. Rotation of the crank arm 28 by the scan motor 30 causes the scan roller 20 at either end thereof to similarly rotate resulting in the scan unit assembly 10 being propelled by the scan rollers 20 through the gas main 18.

Figure 3:
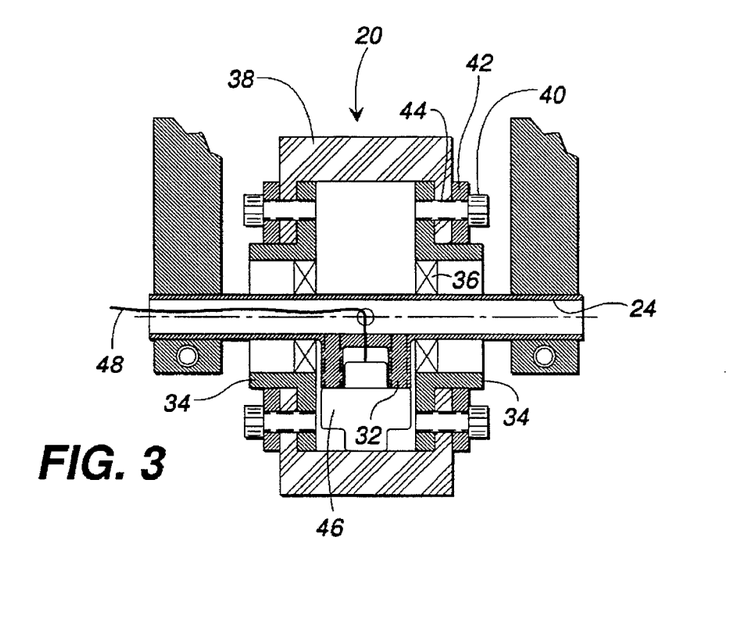
FIG. 3 is a cross-sectional view of the scan roller of the present invention.

Referring now to FIG. 3, a cross-sectional view of a scan roller 20 rotationally mounted to the axle 24 is illustrated. The scan roller 20 includes a hub 32 through which the axle 24 is received and attached thereto, a pair of spaced-apart side plates 34 between which the hub 32 is interposed, a pair of sealed bearings 36 for the rotational mounting of the side plates 34 to the axle 24 and the hub 32, and a polymer tire 38 attached to the side plates 34 by fasteners 40 which are received through a backing plate 42, an inwardly directed lip 44 on the tire 38 and which threadingly engage the side plate 34. An ultrasonic transducer 46 is received within the scan roller 20 and attached to the hub 32 therein. An electrical conductor 48 is connected to the ultrasonic transducer 46 and passes through the axle 24 permitting actuation of the transducer 46 resulting in the production of interrogating ultrasonic pulses which are transmitted through the wall of the tire 38 into the wall of the gas main 18 and the receipt of return pulses from any interfaces encountered by the interrogating pulses. Such interfaces include, but are not limited to, the surface defining the inner diameter of the wall of the gas main, the surface defining the outer diameter of the wall of the gas main, and any imperfections and/or flaws within the wall of the gas main.

Figure 4:
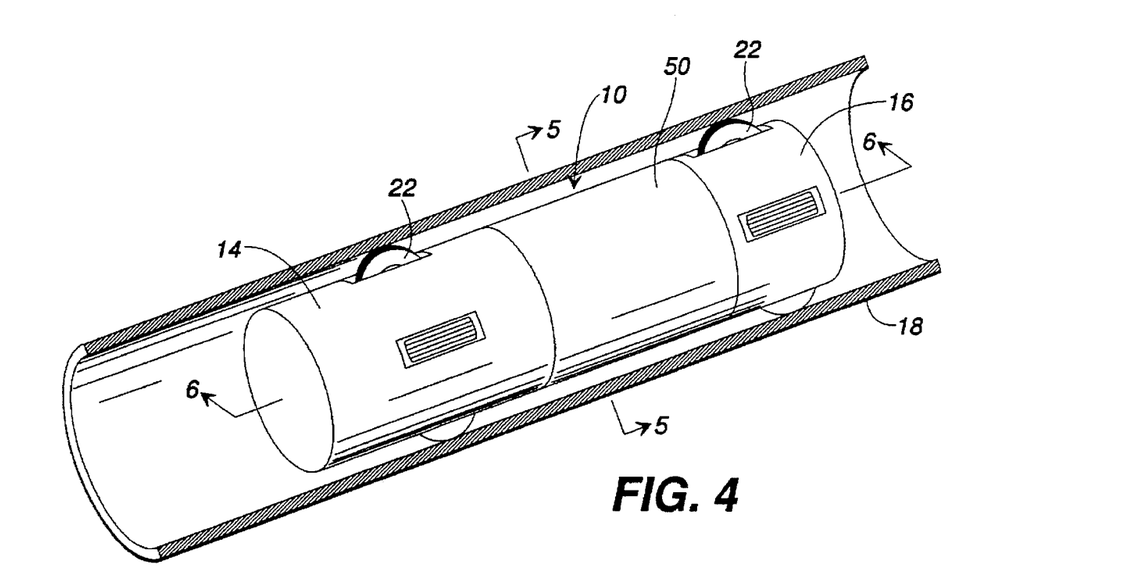
FIG. 4 is a perspective view, partially broken away in cross-section, of an alternate embodiment of the scan unit assembly of the present invention.
Figure 5:
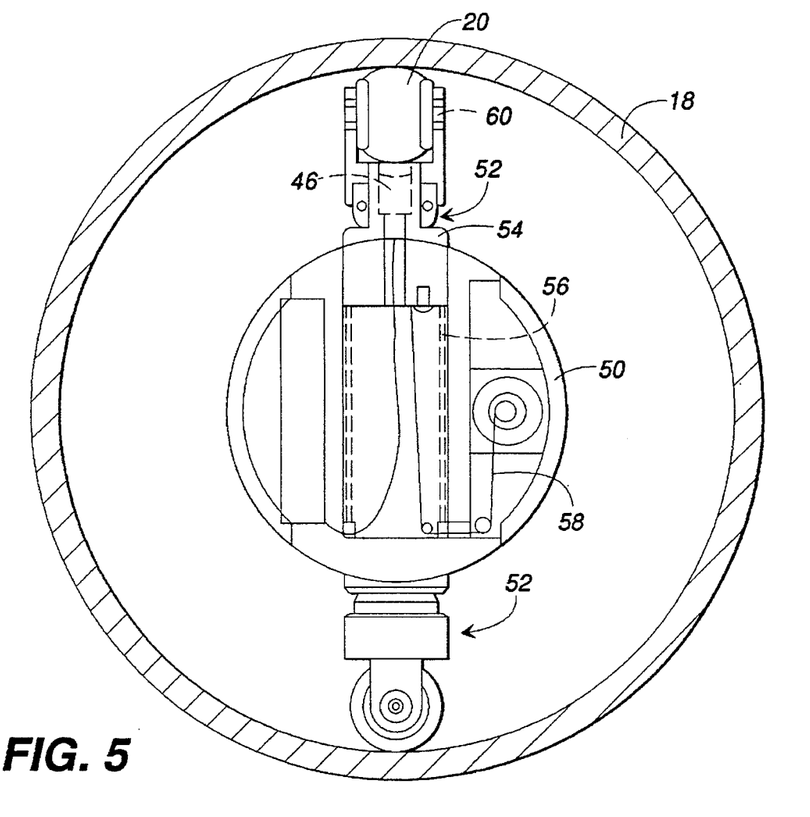
FIG. 5 is a cross-sectional view of the scan unit assembly taken across section-indicating lines 5—5 in FIG. 4.

A perspective view of alternate embodiment of scan unit assembly 10 is shown in FIG. 4. In this embodiment, the scan unit assembly 10 is not self-propelling and requires the application of an externally applied force thereto to propel same through the gas main 18. This embodiment includes a sensor section 50 interposed between the front section 14 and the rear section 16 of the scan unit assembly 10 and rotatable about the longitudinal axis of the scan unit assembly 10. Referring now to FIG. 5, in this embodiment, each scan roller 20 is a part of a scan roller assembly 52, and two scan roller assemblies 52 are received within the sensor section 50 and are angularly positioned approximately 180° relative to one another. Each scan roller assembly 52 is comprised of a telescoping scanning arm 54, a scan roller 20 rotatably connected to one end of the scanning arm 54, an extension spring 56 contacting the other end of the scanning arm 54 and biasing arm 54 radially outwardly from the sensor section 50, and a retraction cable 58 which assists in withdrawing the scanning arm 54 into the sensor section 50. Each retraction cable 58 is connect to a linear variable distance transducer (not shown) which provides information as to the radius of the inner diameter of the gas main 18 as a function of the angular orientation of the scan roller assembly 52. Such information can be utilized to provide data as to the shape and ovality of the inner diameter of the gas main. When the scan roller assemblies 52 are radially extended relative to the sensor section 50, their associated tires 38 grippingly and pliantly engage the surface defining the inner diameter of the wall of the gas main. Conversely, when the scan roller assemblies 52 are in the fully retracted condition, their associated tires 38 are within the sensor section 50. In either embodiment, the tires 38 are formed from a low bulk modulus polymer to provide an optimum mechanical impedance for the passage of ultrasonic pulses therethrough. It should be noted that the ultrasonic transducer 46 might be mounted externally of the scan roller 20, as shown by the dotted outline in FIG. 5. When the transducer 46 is so mounted, the scan roller 20 will be provided without an axle 24, and will be supported for rotation by outwardly directed journals 60 (shown dotted) attached to the side plates 34.

Figure 6:
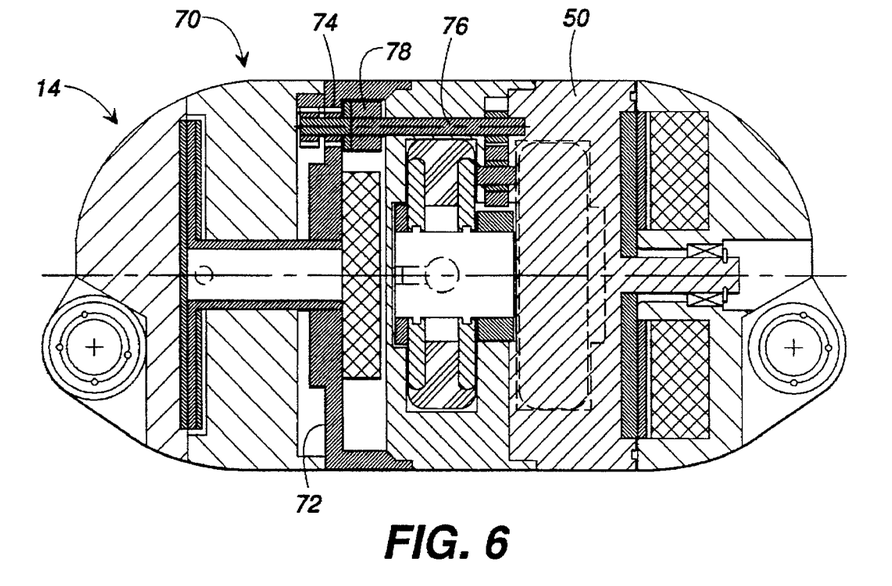
FIG. 6 is a cross-sectional view of the scan unit assembly taken across section-indicating lines 6—6 in FIG. 4 and showing the drive for the sensor section within same.

Referring now to FIG. 6, the drive for the sensor section 50 is illustrated. The drive is comprised of a reversible electric motor 70 located in front section 14 of the scan unit assembly 10. The output shaft of motor 70 is keyed to the sensor section 50 causing rotation thereof. A ring gear 72 is similarly keyed to the output shaft of the motor 70 and engages an idler gear 74 which is connected to a shaft 76 within the sensor section 50 via a ball sprague clutch assembly 78. The shaft 76 is, in turn, connected to two retraction cables 58, each connected to a scanning arm 54. During clockwise rotation of the output shaft of motor 70, the ball sprague clutch assembly 78 is disengaged and the sensor section 50 is rotated by motor 70 and each scanning arm 54 moves radially outwardly under the urging of spring 56 causing its associated tire 38 to contact the surface defining the inner diameter of the wall of the gas main. If an obstruction in the gas main is encountered, the motor 70 is stopped and reversed causing its output shaft to rotate counter-clockwise. In this situation, the ball sprague clutch assembly 78 becomes engaged and the motor 70 "reels-in" the cables 58 causing the scanning arms 54 to retract radially inwardly into the sensor section 50. It should be noted that the wheels 22 on the front section 14 and the rear section 16 of the scan unit assembly 10 prevent rotation of these sections with respect to the sensor section 50 as the scan unit assembly 10 moves through the gas main 18.

Figure 7:
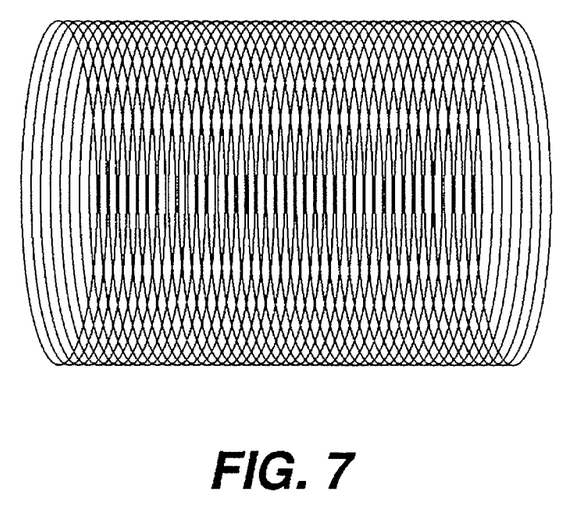
FIG. 7 illustrates the helical scan pattern produced by either embodiment of the scan unit assembly of the present invention.
Figure 8:
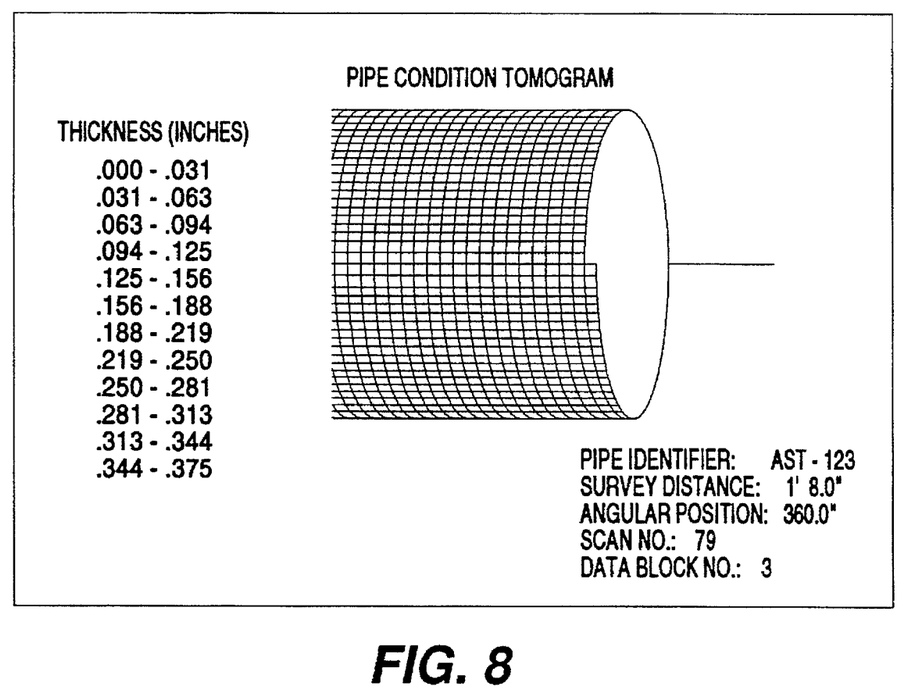
FIG. 8 is a typical tomograph of a gas main produced by either embodiment of the scan unit assembly of the present invention.

As previously indicated, each scan roller 20 has an ultrasonic transducer 46 associated therewith. As tire 38 rotates, the ultrasonic transducer 46 associated therewith produces an interrogating pulse which passes through the tire 38 and intercepts the surfaces defining the inner diameter and the outer diameter of the gas main and any imperfections or flaws within the wall of the gas main. The surfaces defining the inner diameter and the outer diameter of the gas main and any imperfections or flaws within the wall of the gas main, in turn, cause individual return pulses (reflective pulses) to be transmitted back to the ultrasonic transducer 46. As the scan unit assembly 10 moves within the gas main, the tires 38 provide one hundred percent coverage of the wall of the gas main, and a helical scan pattern of same, as illustrated in FIG. 7, is created. It should be noted that such a helical scan pattern is produced by the tire 38 in the either embodiment of the present invention. If the ultrasonic transducer 46 associated with each scan roller 20 is selectively actuated as the scan unit assembly 10 moves within the gas main 18, a model of the wall of the gas main showing wall thickness and sub-surface imperfections, such as cracks, inclusions, flaws or imperfections, can be generated. Each of the sensor sections 12, 50 contains a computer (not shown) which maintains a record of the polar co-ordinates of each interrogating pulse which is transmitted into the wall of the gas main and the return pulses received from the surfaces defining the inner diameter and the outer diameter of the gas main and any imperfections or flaws within the wall of the gas main. Thus, a record is compiled which can be processed into computer generated images of the gas main resulting in a tomograph, similar to that shown in FIG. 8, of the gas main. From such a tomographic image, the surfaces defining the inner and outer diameters of the wall of the gas main and any imperfections or flaws within the wall of the gas main can be examined and accurate physical dimensions of same can be determined.

Figure 9:
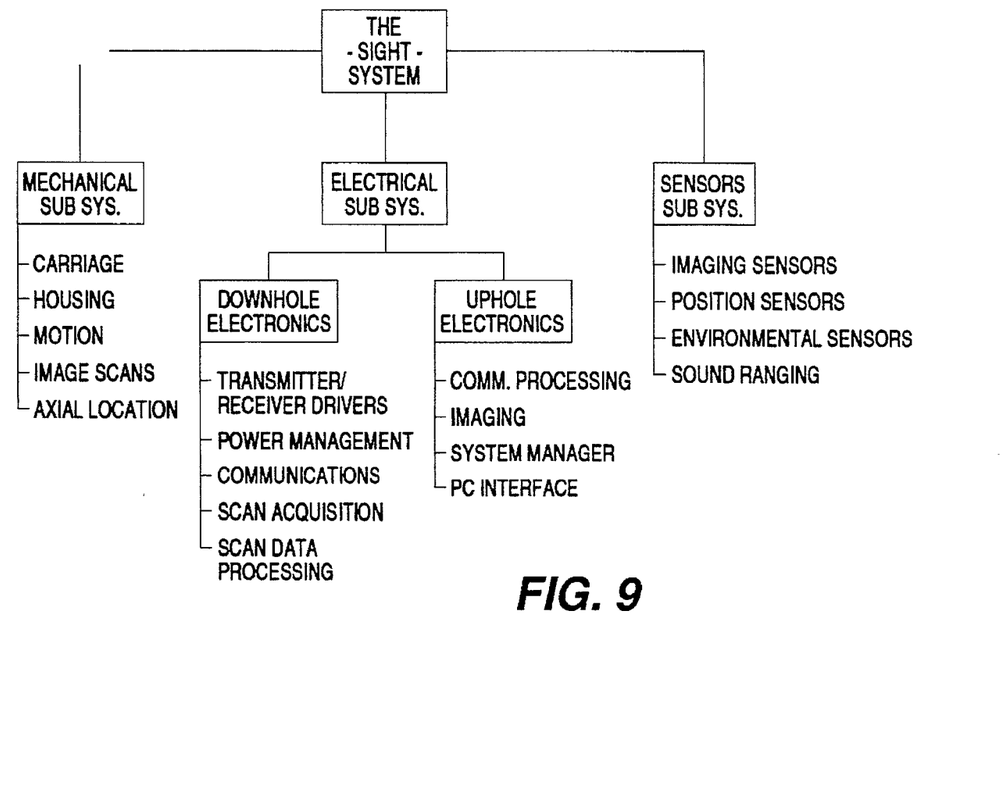
FIG. 9 is a hierarchial diagram of an overall imaging system which can produce tomographs of gas mains, similar to that illustrated in FIG. 8, by utilizing either embodiment of the scan unit assembly of the present invention.

The imaging system utilized by the present invention is comprised of two units, the "downhole" unit, i.e., the scan unit assembly 10, and the surface display unit (not shown). Each of these units is, in turn, comprised of sub-systems, each dedicated to performing a specific function. FIG. 9 is a hierarchial diagram of the overall system identifying the various sub-systems and their respective relationships. With respect to the electrical subsystem, the "downhole" electronics unit, which is within the scan unit assembly 10 and comprised of transmitter/receiver drivers, a power management module, a communication module, a scan acquisition module, and data processing module, is generally responsible for all data acquisition and data transmission to the surface display unit, referred to as the "uphole" electronics unit. The power management module supplies all of the electrical power required by the "downhole" electronics unit. The return pulses from the surfaces defining the inner diameter and the outer diameter of the wall of the gas main and from any imperfections or flaws within the wall are captured by the scan acquisition module, converted into digital form and transmitted to the data processing module for storage and subsequent transmission to the surface display unit ("uphole" electronic unit) via the communication module. The surface display unit handles all data processing, storage and generation of images of the wall of the gas main section being inspected. An umbilical cord (not shown) interconnects the "downhole" electronics unit and the "uphole" electronics unit. Data from the "downhole" electronics unit to the "uphole" electronics unit, and vice versa, is transmitted over the foregoing umbilical cord.

The mechanical sub-system is the scan unit assembly 10. The sensor sub-system is comprised of the ultrasonic transducers 46 associated with each scan roller 20, as well as the position sensors (not shown) within the wheels 22. As previously indicated, the position sensors allow the system to maintain a constant reference in space permitting the accurate "matching" of the tomograph to the location of the scan unit assembly 10 within the gas main 18. It should be noted that environmental sensors, such as temperature and/or noise sensors, can be readily added to the system.

The operation of the system is based upon several principles or definitions. A shot is defined as an interrogating pulse by the ultrasonic transducer 46 that is directed into the wall of the gas main 18 to create return pulses that are used by the system to form tomographic images. The present system utilizes one or more shots, i.e., one or more interrogating pulses, per degree of radial rotation of crank arm 28 or of sensor section 50. The return pulses permit the determination of the following:

1) Radius of the inner diameter of the gas main at the location where the interrogating pulse is received;
2) Radius of the outer diameter of the gas main at the location where the interrogating pulse is received; and
3) The location of imperfections and/or flaws in the wall of the gas main at the location where the interrogating pulse is received.

Figure 10:
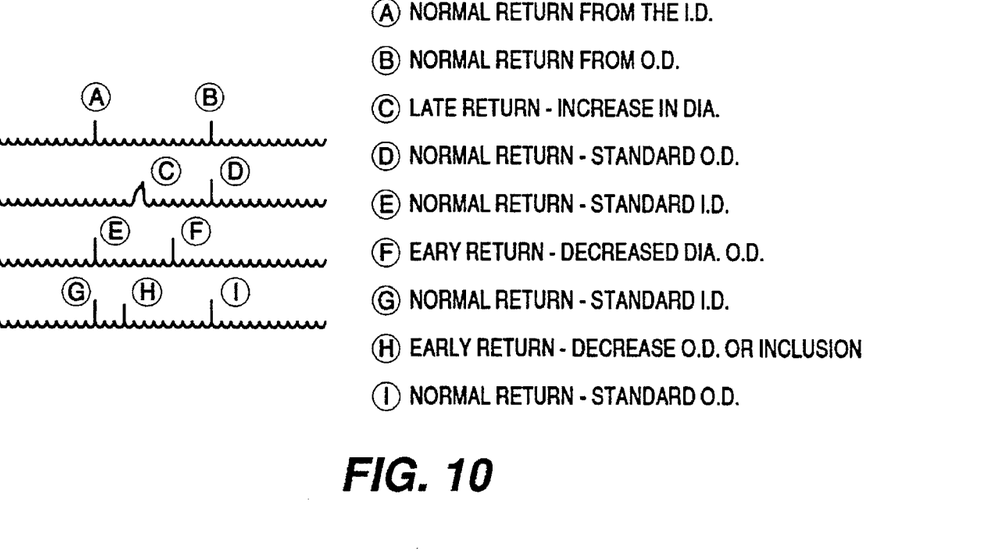
FIG. 10 illustrates typical interrogating pulse patterns produced by either embodiment of the scan unit assembly of the present invention and return pulse patterns produced by the surfaces defining the inner and outer diameters of the gas main and any imperfections or flaws within the wall of the gas main.
Figures 11, 12:
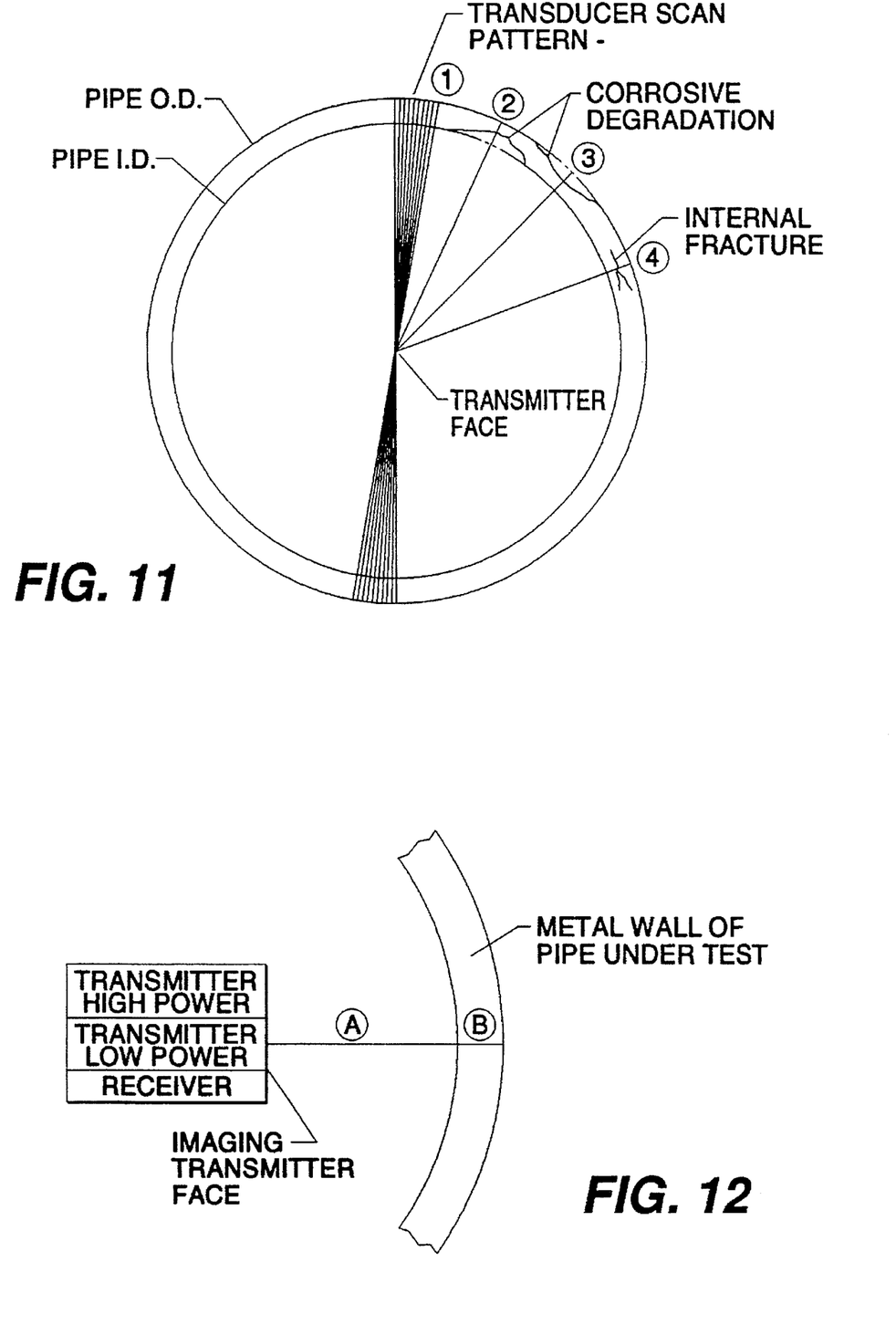
FIG. 11 illustrates a typical scan pattern produced by either embodiment of the scan unit assembly of the present invention.
FIG. 12 illustrates the relationship between the imaging electronics utilized by either embodiment of the present invention and the wall of the gas main.

Referring now to FIG. 10, idealized interrogating pulse patterns and return pulse patterns are illustrated. Pulse A is the normal return pulse from the surface defining the inner diameter of the gas main, whereas pulse B is the normal return pulse from the surface defining the outer diameter of the main. Pulse C is a late return pulse from the surface defining the inner diameter of the main indicating an increase in that diameter, i.e., the wall thickness is decreasing, whereas pulse D is a normal return pulse from the surface defining the outer diameter of the main. Pulse E is a normal return pulse from the surface defining the inner diameter of the main, whereas pulse F is an early return pulse from the surface defining the outer diameter of the main indicating a decrease in that diameter, i.e., the wall thickness of the main is decreasing since the outer diameter is smaller than normal. Pulse G is the normal return pulse from the surface defining the inner diameter of the main, pulse H is an early return pulse indicating a decrease in the outer diameter of the main or an inclusion within the wall of the main, and pulse I is the normal return pulse from the surface defining the outer diameter of the main. Now referring to FIG. 11, a typical scan pattern is illustrated. A scan can be defined as a series of shots taken in sequence over 360° of the inner diameter of the gas main and taken at intervals of one or more shots per one degree of rotation of crank arm 28 or of sensor section 50. Thus, the informational content of a single scan (360° of rotation of crank arm 28 or of sensor section 50) will include the following:

1) A series of values of the inner diameter of the gas main that can be integrated over time to produce a closed curve representing inner diameter of the main;
2) A series of values of the outer diameter of the gas main that can be integrated over time to produce a closed curve representing the outer diameter of the main; and 3) A discontinuous set of values that can be integrated over time and indexed as to radial location to produce lines and shapes representative of imperfections and/or flaws within the wall of the gas main.

A block is defined as 128 scans. Since each scan covers 0.10 axial inches of gas main, the block will represent a sequential composite scan of 128 cross-sectional "slices" arranged side by side for a length of 12.8 inches of gas main. These blocks are stored in the "downhole" computer prior to data transmission, and multiple blocks are stored in sequence for subsequent transmission to the surface display unit.

The ultrasonic transducers 46 that are utilized are of two types. The first type is a low power transducer that provides a short range measurement of the inner diameter of the tire 38. Since this path is virtually noise free, the low power transducer provides an interrogating pulse with minimum reverberation allowing precise measurement of the distance to the inner diameter of the tire 38. The second type of transducer produces interrogating pulses of significantly higher power and is intended to penetrate the surface of the tire 38 and proceed through the wall of the gas main 18 to the outer diameter of the main 18. These latter interrogating pulses need to be of sufficient energy so that the return pulses from the surfaces defining the inner and outer diameter of the wall of the gas main and any imperfections and/or flaws within the wall will be at a level that can be detected. Such high energy interrogating pulses may create significant reverberation noise which can be filtered permitting reception of the return pulses.

Referring now to FIG. 12, the relationship between the imaging electronics utilized by either embodiment of the present invention and the wall of the gas main is illustrated. In this Figure, area A represents the inside of the tire 38 and in which the speed of sound is known and compensated for with respect to temperature. The speed of sound in area A is nominally 4,000 feet per second which is 0.048 inches per microsecond. Area B represents the wall of the gas main being inspected. The speed of sound in this area is 16,400 feet per second or 0.1968 inches per microsecond. From the elapsed time between the initiation of an interrogating pulse and receipt of a return pulse from a surface, various parameters regarding the wall of the gas main can be determined. For example, to determine the outer diameter of the gas main, the elapsed time will be approximately twice the area A and B distances divided by the rate of sound travel in each area, i.e., in each medium. (Two inches of travel in area A requires 41.66 microseconds while 0.5 inches of travel in area B requires 2.54 microseconds.) To determine the inner diameter of the gas main, the elapsed time will be approximately twice the area A distance divided by the rate of sound travel in area A. Furthermore, since the travel time in each area is known, the thickness of the wall of the gas main can be computed from the elapsed time between the return pulse from the surface defining the inner diameter of the main and the return pulse from the surface defining the outer diameter of the main. Similar computations can be made to determine the location of any imperfections or flaws within the wall of the gas main. Thus, the dimensions of the inner and outer diameter of the gas main, the thickness of the wall of the gas main, and the location of any imperfections or flaws within the wall of the gas main can be readily determined through the use of the present invention.

The present invention provides the following inspection capabilities and advantages over presently available inspection apparatus:

a) One hundred percent inspection of the wall of the gas main;

b) Can be utilized on all types of gas main material, such as steel, cast iron and plastic (polyethylene) piping;

c) Can be used for gas mains of various inner diameters;

d) Uses a well-proven technology, i.e., ultrasonic inspection techniques;

e) Provides an accurate, readily interpretable visual display of the condition of the gas main;

f) Permits measurement of the thickness of the wall of the gas main and permits identification of imperfections and/or flaws and the location of same within the wall of the main; and g) The inspection system poses no safety risks.

Certain modifications and improvements will occur to those skilled in the art upon reading the foregoing. It should be understood that all such modifications and improvements have not been included herein for the sake of conciseness and readability, but are properly within the scope of the following claims.

We claim:

1. An apparatus for inspecting surfaces and a cross-section of the wall of a cylindrical object having a longitudinal length, said apparatus comprising a sensor which contacts one of the surfaces of the wall of the object being inspected, said apparatus further comprising a means for rotating said sensor in a path permitting said sensor to traverse said contacted surface of the object being inspected and maintain contact with said contacted surface over the longitudinal length of the object, said sensor comprising a roller having an outside surface which contacts said contacted surface of the wall of the object being inspected and an inside surface concentric with said outside surface wherein said outside surface and said inside surface form a wall of said roller, and an ultrasonic transducer adjacent said wall of said roller for transmitting interrogating pulses through said wall of said roller into the wall of the object being inspected and receiving return pulses from interfaces encountered by said interrogating pulses.

2. The apparatus as defined in claim 1 wherein said ultrasonic transducer is positioned within said roller and oriented so that said ultrasonic transducer is in contact with said inside surface of said tire.

3. The apparatus as defined in claim 1 wherein said ultrasonic transducer is positioned external of said roller and orientated to be in contact with said outside surface of said roller opposite a portion of said outside surface of said roller in contact with said contacted surface.

4. The apparatus as defined in claim 1 wherein said interrogating pulses are transmitted by said ultrasonic transducer into the wall of the object being inspected at a pre-determined spaced-apart interval.

5. The apparatus as defined in claim 1 wherein said path through which said sensor traverses is a helical path.

6. The apparatus as defined in claim 1 wherein said contacted surface is the inner surface of the cylindrical object being inspected.

7. The apparatus as defined in claim 1 wherein said rotating means comprises a housing in which said sensor is received, and means for rotating said housing causing rotation of said sensor.

8. The apparatus as defined in claim 7 wherein more than one said sensor is received within said housing and are positioned in a predetermined orientation.

9. The apparatus as defined in claim 8 wherein said predetermined orientation of said sensors results in the spacing between each pair of adjacent sensors to be substantially the same.

10. The apparatus as defined in claim 7 further including means for biasing said sensor radially outwardly with respect to said housing.

11. The apparatus as defined in claim 10 wherein said biasing means is a spring received within said housing and oriented therein to operatively contact said sensor.

12. The apparatus as defined in claim 7 further including means for retracting said sensor radially inwardly into said housing.

13. The apparatus as defined in claim 1 further including a plurality of wheels positioned adjacent the front of said apparatus and adjacent the rear of said apparatus, said plurality of wheels positioning said apparatus within the cylindrical object being inspected.

14. The apparatus as defined in claim 13 wherein said plurality of wheels at each end of said apparatus are positioned in a pre-determined orientation.

15. The apparatus as defined in claim 14 wherein said pre-determined orientation of said wheels results in the spacing between each pair of adjacent wheels to be substantially the same.

16. The apparatus as defined in claim 1 further including display means for transmitting said return pulses to said display means to provide a visual indication of said contacted surfaces defining the wall of the cylindrical object being inspected and the cross-section of said wall.

17. An apparatus for inspecting surfaces and cross-section of the wall of a cylindrical object having a longitudinal length, said apparatus comprising:

a sensor which contacts one of the surfaces of the wall of the object being inspected; means for rotating said sensor in a path permitting said sensor to traverse said contacted surface of the object being inspected and maintain contact with said contacted surface over the longitudinal length of the object, said rotating means comprising a housing in which said sensor is received, and means for rotating said housing causing rotation of said sensor; and means for retracting said sensor radially inwardly into said housing, said retracting means operatively connected to said rotating means.

18. The apparatus as defined in claim 17 wherein said retracting means comprises a cable operatively connected to said sensor and to said rotating means.

* * * * *